United States Patent
Hollander

(10) Patent No.: US 11,712,165 B2
(45) Date of Patent: Aug. 1, 2023

(54) SMARTPHONE SOFTWARE-BASED MEASUREMENT OF CYANOSIS AND CAPILLARY REFILL TIME

(71) Applicant: Eric Jonathan Hollander, Beverly Hills, CA (US)

(72) Inventor: Eric Jonathan Hollander, Beverly Hills, CA (US)

(*) Notice: Subject to any disclaimer, the term of this patent is extended or adjusted under 35 U.S.C. 154(b) by 413 days.

(21) Appl. No.: 17/025,075

(22) Filed: Sep. 18, 2020

(65) Prior Publication Data

US 2022/0087538 A1 Mar. 24, 2022

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0077* (2013.01); *A61B 5/0261* (2013.01); *A61B 5/1032* (2013.01); *A61B 5/14551* (2013.01); *A61B 5/412* (2013.01); *A61B 5/4845* (2013.01); *A61B 5/4875* (2013.01); *A61B 5/7221* (2013.01); *A61B 5/7267* (2013.01); *A61B 5/742* (2013.01); *A61B 5/748* (2013.01); *G06N 3/04* (2013.01); *G06N 3/08* (2013.01); *G06T 7/0012* (2013.01); *G06T 7/20* (2013.01); *G06T 7/70* (2017.01); *G06T 7/90* (2017.01); *G06V 40/107* (2022.01); *G16H 10/60* (2018.01);
(Continued)

(58) Field of Classification Search
CPC . A61B 5/1032; A61B 5/0077; A61B 5/02028; A61B 5/14551; A61B 5/748; A61B 5/0205; A61B 5/7267; A61B 5/02416; G06T 7/0012; G06T 2207/10016; G06T 7/90; G06T 2207/30196; G06V 2201/03; G06V 10/82; G06V 40/107; G06V 40/14; G06V 10/56; G06V 10/25; G06V 40/117; G06V 40/11; G16H 50/20; G16H 10/60; G06N 3/08; G06N 3/045
See application file for complete search history.

(56) References Cited

U.S. PATENT DOCUMENTS 5,899,855 A * 5/1999 Brown .................... G16H 40/67
128/920
2018/0103873 A1* 4/2018 Jacquet-Lagreze ..........................
A61B 5/0077
(Continued)

*Primary Examiner* — Eric F Winakur
*Assistant Examiner* — Elina Sohyun Ahn

(57) ABSTRACT

A system for measuring blood oxygenation levels and capillary refill time (CRT) of a user includes a camera configured to capture a video stream that includes a series of images representing a process of first squeezing a fingernail of the user to a blanched state, and then releasing to a resting state, and a Convolutional Neural Network (CNN) based processing unit configured to process an input image to create a two-dimensional representation of features, remove spatial relationships in the two-dimensional representation, generate non-spatial metadata, identify the fingernail in the resting state, and regions within a static image of the fingernail, and configured to generate a blood oxygenation value, and a measurement confidence level, and generate a CRT value of the user by applying the blood oxygenation value, and the measurement confidence level to a series of images captured by the camera over time.

19 Claims, 12 Drawing Sheets

(51) Int. Cl.
*A61B 5/026* (2006.01)
*A61B 5/1455* (2006.01)
*A61B 5/103* (2006.01)
*G16H 40/67* (2018.01)
*G16H 50/20* (2018.01)
*G16H 50/30* (2018.01)
*G16H 10/60* (2018.01)
*G06N 3/04* (2023.01)
*G06N 3/08* (2023.01)
*G06T 7/00* (2017.01)
*G06T 7/20* (2017.01)
*G06T 7/70* (2017.01)
*G06T 7/90* (2017.01)
*G06V 40/10* (2022.01)

(52) U.S. Cl.
CPC ............. *G16H 40/67* (2018.01); *G16H 50/20* (2018.01); *G16H 50/30* (2018.01); *A61B 2560/0252* (2013.01); *G06T 2200/24* (2013.01); *G06T 2207/10016* (2013.01); *G06T 2207/20084* (2013.01); *G06T 2207/30196* (2013.01); *G06V 2201/03* (2022.01)

(56) References Cited

U.S. PATENT DOCUMENTS

2018/0271382 A1* 9/2018 Bezemer .............. A61B 5/6898
2020/0121256 A1* 4/2020 McDuff ................ G16H 50/20

* cited by examiner

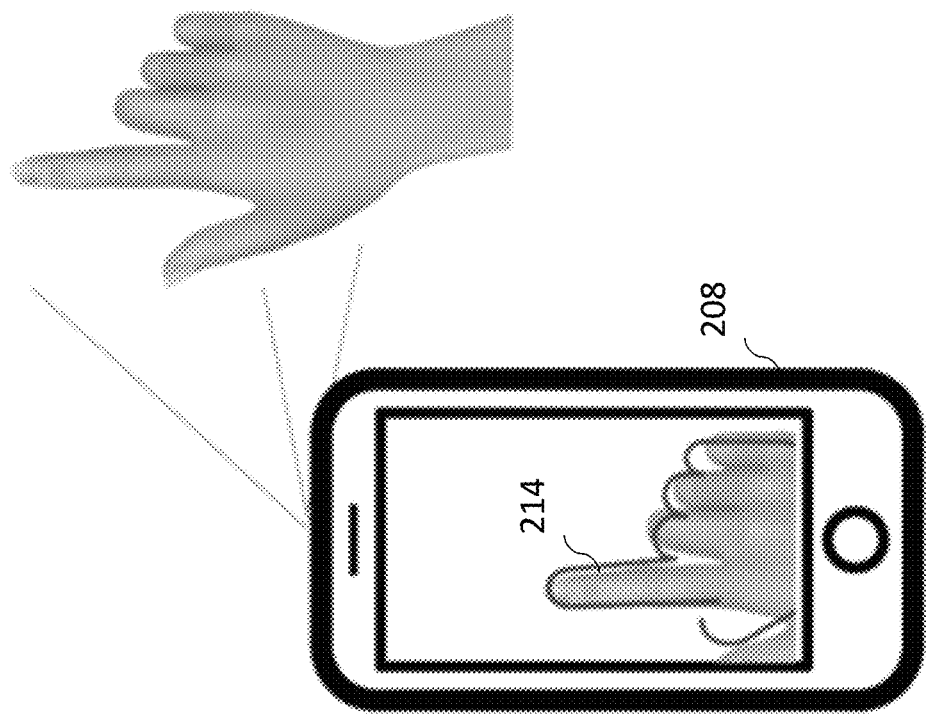
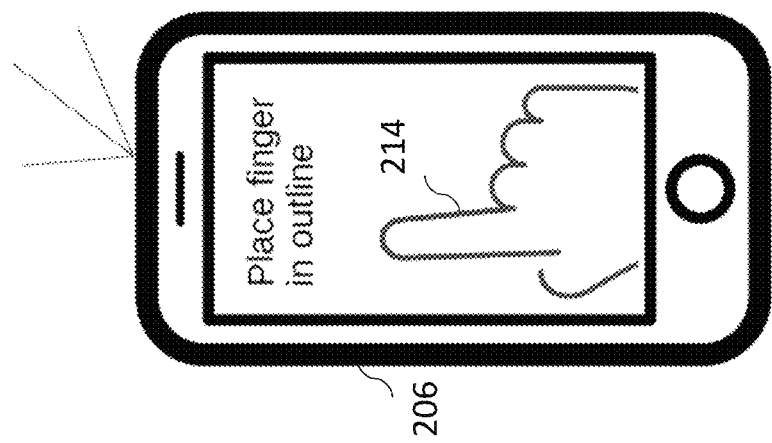
FIG.2D
FIG.2C

SMARTPHONE SOFTWARE-BASED MEASUREMENT OF CYANOSIS AND CAPILLARY REFILL TIME

FIELD OF THE DISCLOSURE

The present disclosure relates generally to the field of health monitoring and medical diagnosis, and more particularly to systems and methods for quantitatively evaluating blood circulation in the extremities and blood oxygenation.

BACKGROUND

Low blood oxygen levels are associated with various serious health conditions. The person experiencing low blood oxygen may not be aware of it in the early stages. Many common conditions, such as common cold, have the same symptoms as some other more dangerous conditions, such as Coronavirus Disease 2019 (COVID-19). One of the observable manifestations of low blood oxygen is called cyanosis, which refers to a bluish tint of the skin, from the color cyan, a blue-green color. In severe cases, an individual with light skin can have a readily visible bluish tint to the skin on various areas of the body, including the fingertips, fingernails, tongue, and even the face and other regions. In mild cases, or in individuals with darker skin color, cyanosis is difficult to see in the face, but can be seen in areas where the skin is thin and is not pigmented. One such area is under fingernail, which has capillaries close to the surface and lacks pigmentation, even in individuals with dark skin colors.

Cyanosis in infants may indicate serious problems. Infants may have cyanosis and are not able to inform others about what they are experiencing. Also, exposure to certain chemicals may cause cyanosis. At low levels, the individual may not be aware of the effects of the exposure, but the effect could be detected by checking blood oxygen levels by evaluating cyanosis. This could be useful in emergency situations such as an industrial accident. It could also be useful as part of a toolkit for response to possible use of chemical weapons against civilians, who do not usually have equipment for detecting chemical weapons or measuring blood oxygen.

Cyanosis may be a manifestation of certain chronic health conditions as well, and individuals experiencing these conditions may not be aware of it and so may delay getting treatment. For example, conditions of chronic obstructive pulmonary disease (COPD), pulmonary embolism, congestive heart failure, and others, may give rise to cyanosis before the patient is aware of the disease occurring. Early indications of such conditions may lead to earlier and more effective treatment, especially if the individual can check himself easily outside of a clinical setting.

An important medical examination is the peripheral vascular examination (PVE). Various health conditions, such as diabetes, shock, dehydration, and hypothermia may result in reduced blood flow to the extremities. COVID-19 is a recent disease which has an unusual feature of causing increased clotting activity and therefore decreased blood flow in the extremities. A complete medical PVE involves a medical professional taking the patient through a series of steps and making observations and measurements. One key step of the PVE is the capillary refill time (CRT) measurement, in which the fingernail or fingertip is squeezed, removing the blood from the capillaries. This condition is called "blanched", in reference to the white appearance of the flesh without blood in the capillaries. The fingernail or fingertip is released, and blood returns to the capillaries as it is pushed by the circulatory system. As with cyanosis observations, in dark skinned individuals, the fingernail beds are ideal because they are not pigmented. The time of return of blood is measured in seconds by a clinician making a visual observation. The time to go from the blanched state to the normal state is called the CRT. Different medical training sources specify either two or three seconds as normal values for the CRT. A prolonged CRT value may be a sign of acute conditions, such as shock, hypothermia, and dehydration, or chronic problems with peripheral circulation. A human observer of the capillary refill process is limited by human inaccuracy in timing such short intervals, and the subjective observation of when the normal state is reached.

SUMMARY

In an aspect of the present disclosure, there is provided a system for measuring blood oxygenation levels and capillary refill time (CRT) of a user using a mobile computing device. The system includes a camera configured to capture a video stream of a user, wherein the video stream includes a series of images representing a process of first squeezing a fingernail of the user to a blanched state, and then releasing the fingernail to a resting state, and a Convolutional Neural Network (CNN) based processing unit that includes a pre-trained CNN. The pre-trained CNN includes an input layer configured to receive one or more input images from the camera in form of three-dimensional tensors, a plurality of convolutional and pooling layers configured to process an input image to create a two-dimensional representation of one or more features, a flattening layer configured to remove spatial relationships in the two-dimensional representation and generate non-spatial data, a neural network based metadata processing module configured to generate non-spatial metadata for the user based on a metadata vector, a concatenation layer configured to concatenate non-spatial metadata with the non-spatial data generated by the flattening layer, a plurality of fully connected layers and an output layer. The fully connected layers are configured to identify the fingernail in the resting state, and one or more regions within a static image of the fingernail, and correlate one or more non-spatial features with one or more pre-defined blood oxygenation values, and an output layer configured to generate a blood oxygenation value indicating blood oxygenation levels in the user, and a measurement confidence level indicating an extent of success of measurement. The output layer is configured to generate a CRT value of the user by applying the blood oxygenation value, and the measurement confidence level to a series of images captured by the camera over time, wherein the CRT corresponds to time lapsed from the blanched state to the resting state of the fingernail. The system further includes an output display device for displaying the blood oxygenation and CRT values to the user, and generating one or more pre-defined alerts corresponding to the displayed blood oxygenation and CRT values.

In another aspect of the present disclosure, there is provided a method for measuring blood oxygenation levels and capillary refill time (CRT) of a user using a mobile computing device. The method includes capturing a video stream of a user, wherein the video stream includes a series of images representing a process of first squeezing a fingernail of the user to a blanched state, and then releasing the fingernail to a resting state, and receiving one or more input images from the camera in form of three-dimensional tensors. The method may further include processing an input image to create a two-dimensional representation of one or more features, and removing spatial relationships in the two-dimensional representation and generate non-spatial data. The method may further include generating non-spatial metadata for the user based on a metadata vector, and concatenating non-spatial metadata with the non-spatial data generated by the flattening layer. The method may further include identifying the fingernail in the resting state, and one or more regions within a static image of the fingernail, and correlating one or more non-spatial features with one or more pre-defined blood oxygenation values, and generating a blood oxygenation value indicating blood oxygenation levels in the user, and a measurement confidence level indicating an extent of success of measurement. The method may further include generating a CRT value of the user by applying the blood oxygenation value, and the measurement confidence level to a series of images captured by the camera over time, wherein the CRT corresponds to time lapsed from the blanched state to the resting state of the fingernail. The method may further include displaying the blood oxygenation and CRT values to the user, and generating one or more pre-defined alerts corresponding to the displayed blood oxygenation and CRT values.

In yet another aspect of the present disclosure, there is provided a non-transitory computer readable medium configured to store a program causing a computer to measure blood oxygenation levels and capillary refill time (CRT) of a user using a mobile computing device. The program is configured to capture a video stream of a user, wherein the video stream includes a series of images representing a process of first squeezing a fingernail of the user to a blanched state, and then releasing the fingernail to a resting state. The program may be further configured to receive one or more input images from the camera in form of three-dimensional tensors, and process an input image to create a two-dimensional representation of one or more features. The program may be further configured to remove spatial relationships in the two-dimensional representation and generate non-spatial data, and generate non-spatial metadata for the user based on a metadata vector. The program may be further configured to concatenate non-spatial metadata with the non-spatial data generated by the flattening layer, identify the fingernail in the resting state, and one or more regions within a static image of the fingernail, and correlate one or more non-spatial features with one or more pre-defined blood oxygenation values. The program may be further configured to generate a blood oxygenation value indicating blood oxygenation levels in the user, and a measurement confidence level indicating an extent of success of measurement, and generate a CRT value of the user by applying the blood oxygenation value, and the measurement confidence level to a series of images captured by the camera over time, wherein the CRT corresponds to time lapsed from the blanched state to the resting state of the fingernail. The program may be further configured to display the blood oxygenation and CRT values to the user, and generate one or more pre-defined alerts corresponding to the displayed blood oxygenation and CRT values.

Various embodiments of the present disclosure use smartphones or similar devices with cameras, and a novel user interface, to capture images of the fingernail bed to measure cyanosis, CRT, or both. The present invention may be completely operational on a smartphone, in which the image analysis is done on the smartphone, or the images may be sent to a server (the cloud) for analysis, or a combination of both. The present invention may be a self-contained tool that may be integrated into other health or wellness applications. The present invention may send data to a server which gathers health information about individual patients and may be integrated into a broader telehealth system. For example, the CRT value may be transmitted to a tele-health server, so as to enable the healthcare providers to do the follow-up with the patient, if necessary.

In an embodiment of the present disclosure, the oxygenation levels of blood may be communicated to other health alert and reporting systems, such as tele-health applications and service providers. For example, during a pandemic, users who are concerned or are feeling symptoms may use the mobile application, and would report their symptoms. By having both self-reported symptoms, such as cough, aches, or sneezing, as well as blood oxygen levels, non-serious issues such as allergies or a cold could be distinguished from serious issues such as COVID-19 or a chemical exposure. For example, changes in fingernail color could be correlated with later diagnosis of COVID-19 to allow more precise early-stage tele-health diagnosis of the condition. This distinction would save a user from having to go to a clinic, possibly being exposed to illness or creating a burden on staff. The mobile application could be used a general health monitoring app for patients who have health conditions but want to reduce the need to travel to clinics, such as patients with circulatory or lung conditions.

In another embodiment of the present disclosure, the server may allow an entity to monitor the health status of a population and discern trends. In an example, a network-linked carbon monoxide detector could send an alert to its respective server which would pass the alert on to users to inform them that they should check with the mobile application immediately. An individual who has been exposed to carbon monoxide (CO), but at a level below where symptoms such as drowsiness, and confused mental state are obvious, could check his own CO level by using the techniques disclosed herein.

BRIEF DESCRIPTION OF DRAWINGS

The following detailed description of the preferred embodiments of the present disclosure will be better understood when read in conjunction with the appended drawings. The present disclosure is illustrated by way of example, and not limited by the accompanying figures, in which like references indicate similar elements.

FIGS. 2A-2F illustrate first through sixth exemplary screenshots of the mobile computing device for testing cyanosis using a static image of the fingernail of the user in its normal state;

DETAILED DESCRIPTION

The detailed description of the appended drawings is intended as a description of the currently preferred embodiments of the present disclosure, and is not intended to represent the only form in which the present disclosure may be practiced. It is to be understood that the same or equivalent functions may be accomplished by different embodiments that are intended to be encompassed within the spirit and scope of the present disclosure.

As used in the specification and claims, the singular forms "a", "an" and "the" include plural references unless the context clearly dictates otherwise. For example, the term "an article" may include a plurality of articles unless the context clearly dictates otherwise.

Those with ordinary skill in the art will appreciate that the elements in the figures are illustrated for simplicity and clarity and are not necessarily drawn to scale. For example, the dimensions of some of the elements in the figures may be exaggerated, relative to other elements, in order to improve the understanding of the present disclosure.

There may be additional components described in the foregoing application that are not depicted on one of the described drawings. In the event, such a component is described, but not depicted in a drawing, the absence of such a drawing should not be considered as an omission of such design from the specification.

As required, detailed embodiments of the present disclosure are disclosed herein; however, it is to be understood that the disclosed embodiments are merely exemplary of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Further, the terms and phrases used herein are not intended to be limiting but rather to provide an understandable description of the disclosure.

Figure 1:
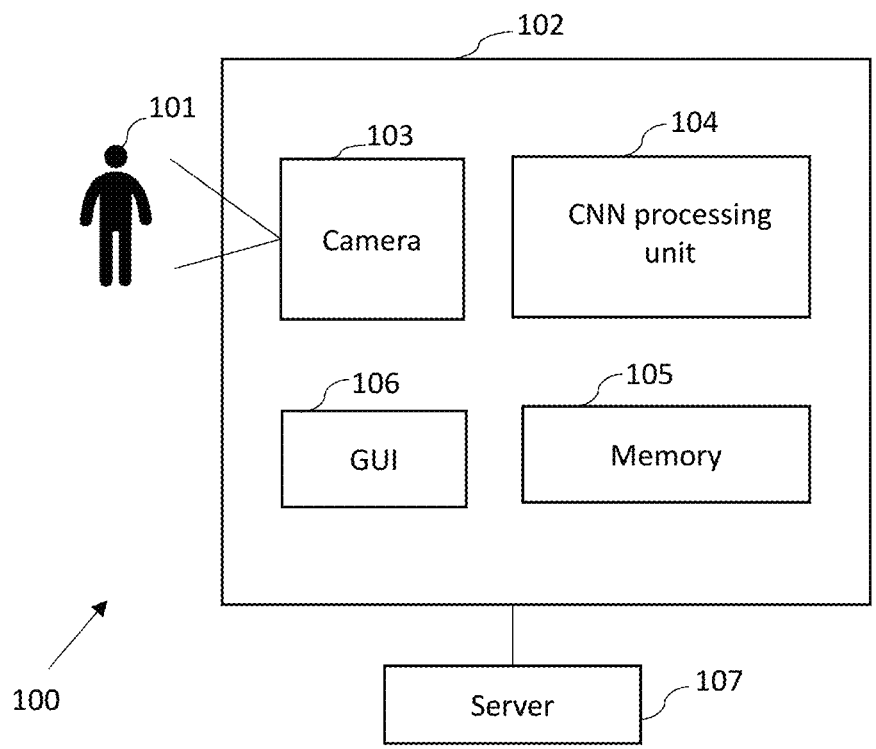
FIG. 1 illustrates an environment wherein various embodiments of the present invention can be practiced.
Figure 2B:
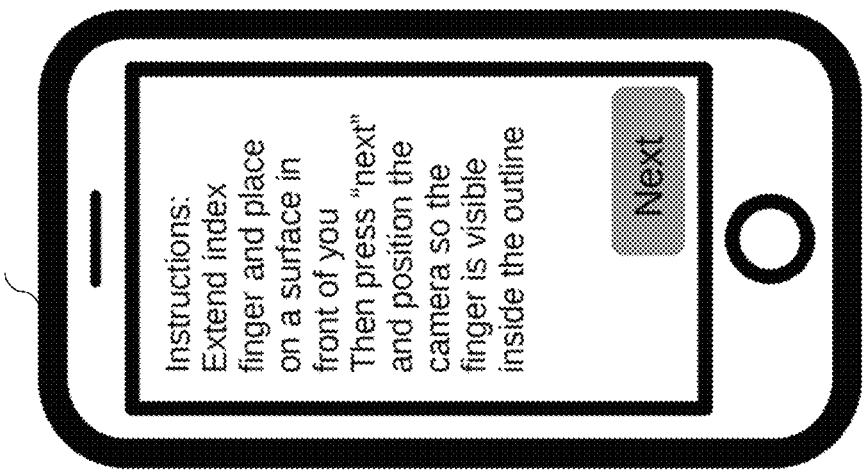
Figure 2A:
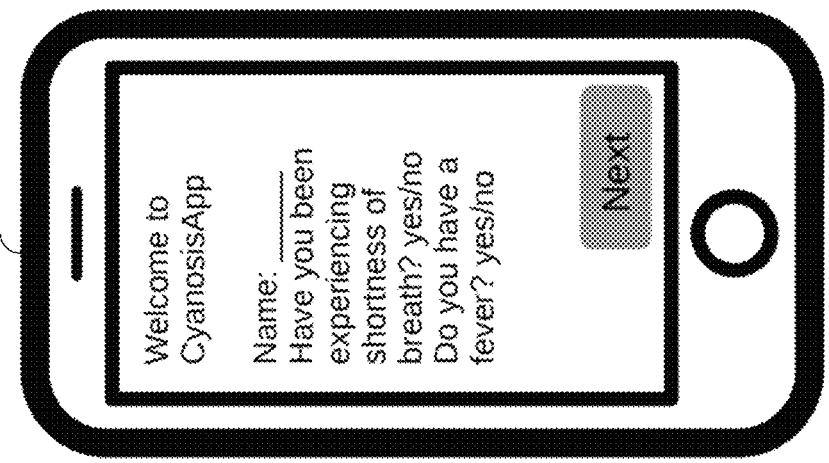
Figure 2F:
Figure 2E:
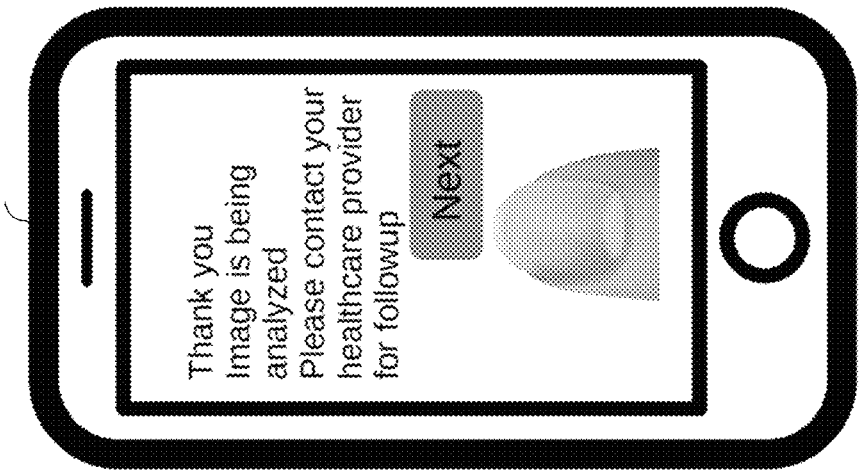
Figure 3A:
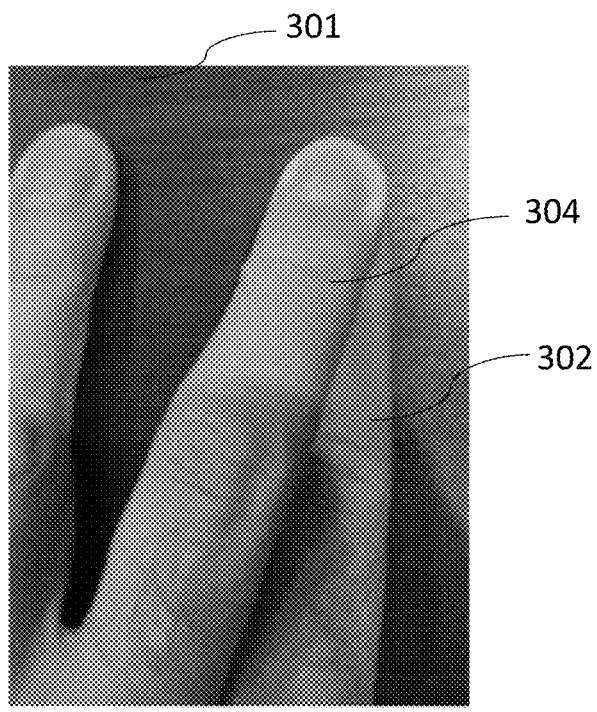
FIGS. 3A-3E illustrate a brief video stream used by the CRT measurement module for measuring CRT of the user, in accordance with an embodiment of the present disclosure.
Figure 3B:
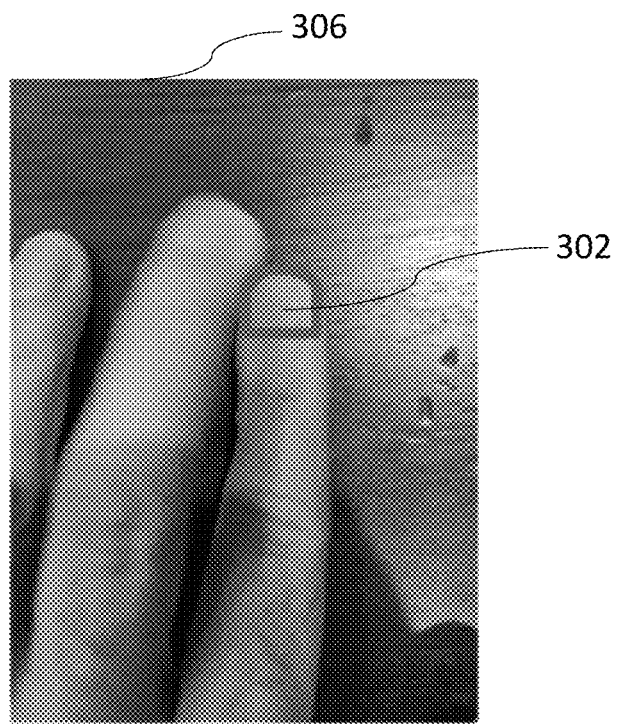
Figure 3C:
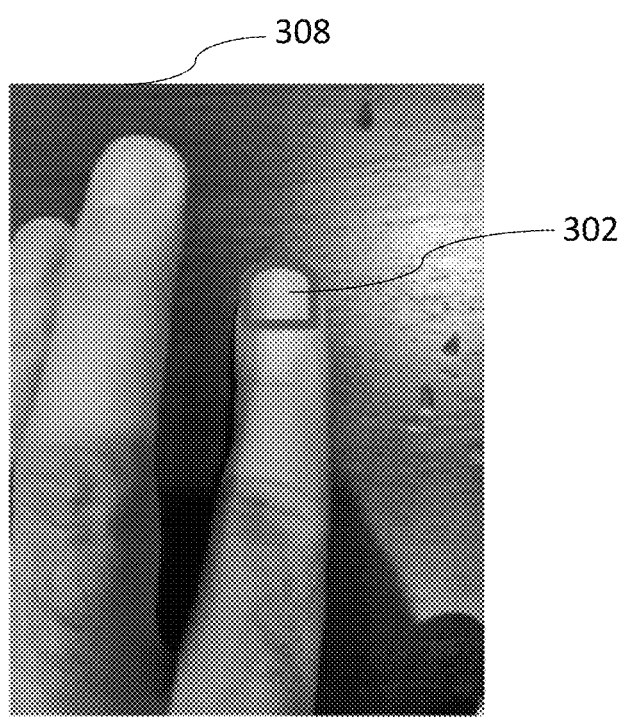
Figure 3D:
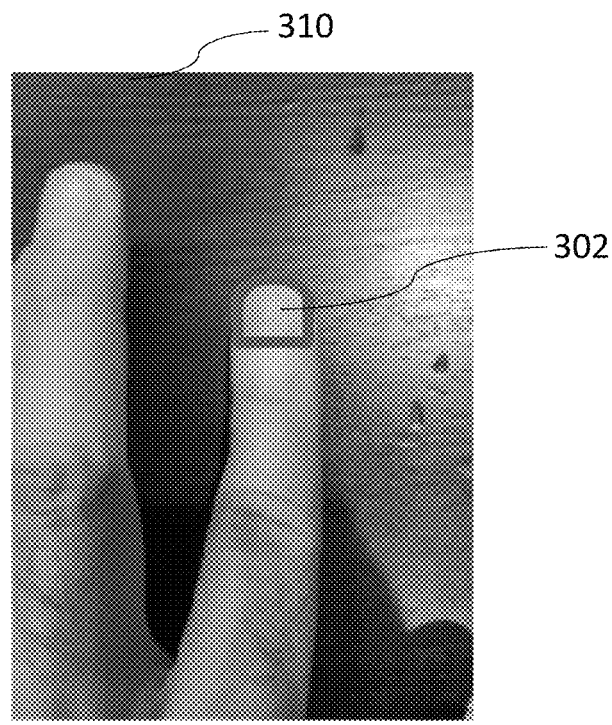
Figure 3E:
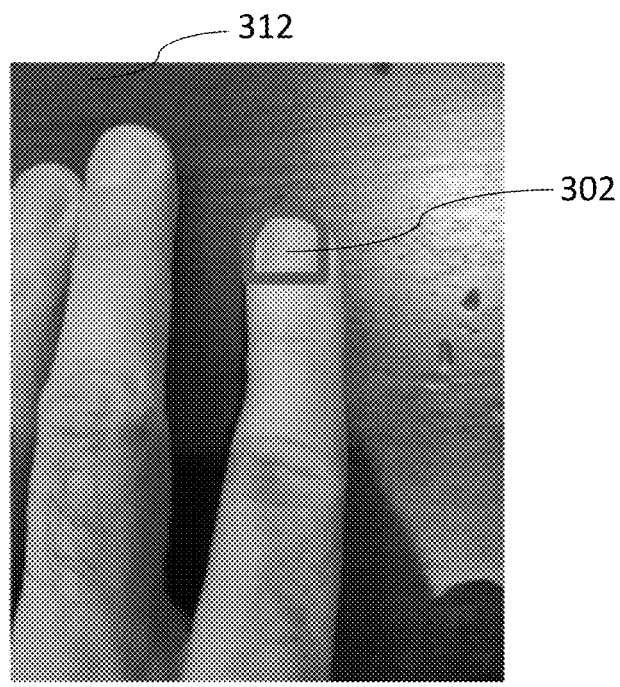

FIG. 1 illustrates an environment 100 wherein various embodiments of the present invention can be practiced. The environment 100 includes a user 101, and a mobile computing device 102 for analyzing blood oxygen levels of the user 101. In the context of the present disclosure, the user 101 is a non-expert, and an ordinary person with no special training of analyzing blood oxygen levels. The mobile computing device 102 is a mobile device that includes a high-quality camera 103, a Convolutional Neural Network (CNN) processing unit 104 with high levels of computational power, and a Graphical User interface (GUI) 106. Examples of the mobile computing device 102 include, but are not limited to a smartphone, an iPad, and the like.

The CNN processing unit 104 may be implemented as one or more microprocessors, microcomputers, microcontrollers, digital signal processors, logic circuitries, and/or any devices that manipulate data based on operational instructions. The CNN processing unit 104 is configured to fetch and execute computer-readable instructions and one or more routines stored in a memory 105. The memory 105 may include any non-transitory storage device including, for example, volatile memory such as RAM, or non-volatile memory such as EPROM, flash memory, and may store one or more computer-readable instructions or routines.

The CNN processing unit 104 may be implemented as a combination of hardware and programming (for example, programmable instructions) to implement one or more functionalities thereof. The programming for the processing unit 104 may be processor executable instructions stored on a non-transitory machine-readable storage medium and the hardware for the processing unit 104 may include a processing resource (for example, one or more processors), to execute such instructions.

The camera 103 is configured to capture a video stream of the user 101, wherein the video stream includes a series of images representing a process of first squeezing a fingernail to a blanched state, and then releasing the fingernail to a resting state. The CNN processing unit 104 is configured to automatically detect a fingernail and enable capturing an image of the fingernail, measure the CRT of the user using machine learning vision and learning from a training corpus to estimate a curve of transition from the blanched state to the resting state of the fingernail. The processing unit 104 is further configured to detect cyanosis in the user based on an image of the fingernail in the resting state by identifying the fingernail and one or more regions within the fingernail image, and correlate visual features of the one or more regions with blood oxygen levels of the user to detect cyanosis, wherein cyanosis is defined as a bluish tint of the blood observed in the capillaries. The CNN processing unit 104 implements computer vision algorithms (explained later) that may make measurements very accurately based on images, due to the large amount of color information in the camera 103 of the mobile computing device 102.

In an embodiment of the present disclosure, the CNN processing unit 104 may be configured to indicate other health problems such as carbon monoxide (CO) poisoning. In particular, carbon monoxide causes blood to become excessively red, as the carbon monoxide molecule binds to hemoglobin more strongly than oxygen and so the individual's hemoglobin may no longer carry oxygen and remains in a reddish state even in the capillaries. An individual exposed to CO may become confused, sleepy, and eventually pass out and can suffer brain damage and death. Upon CO poisoning, the blood does not become blue tinted, but rather becomes an unnatural red color and stays that way as it passes through the capillaries, whereas hemoglobin carrying oxygen would release the oxygen in the capillaries and would lose the reddish color. When the CNN processing unit 104 detects that the blood has been affected with CO, it may be configured to generate an alert for the user regarding the actions to be taken, and also alert corresponding tele-health healthcare providers.

In an embodiment of the present disclosure, the CNN processing unit 104 is configured to run a mobile application on the mobile computing device 102 for analyzing blood oxygen levels and CRT of the user 101. The mobile application has the Graphical User interface (GUI) 106 that is configured to receive inputs from the user 101, as well as provide instructions/output to the user 101 pertaining to analysis of blood oxygen levels and CRT. In an embodiment of the present disclosure, the GUI 106 may capture an image of the user 101, and send to a server 107 for analysis. The transmission to the server 107 is by a secure communication channel such as Transport Layer Security (TLS), to protect patient privacy and comply with medical privacy regulations (HIPAA). In another embodiment of the present disclosure, the analysis is performed locally at the processing unit 104. The mobile application may be further configured to display the blood oxygenation and CRT values to the user, and generate one or more pre-defined alerts corresponding to the displayed blood oxygenation and CRT values. In an example, an alert may be generated for the user, if the displayed CRT value exceeds a given threshold value, such as 2 seconds.

FIGS. 2A-2F illustrate first through sixth exemplary screenshots 202 till 212 of the mobile computing device 102 for testing cyanosis using a static image of the fingernail of the user 101 in its normal state.

The first screenshot 202 shows an introductory page of the GUI 106 shown in FIG. 1, in accordance with an embodiment of the present disclosure. The introductory page appears when the user activates the mobile application on the mobile computing device 102 of FIG. 1. As shown in FIG. 1, the introductory page enables the user 101 to enter their name and other information, and may enable the user 101 to go through other screens to capture other symptoms information. The introductory page may include a login step for security purposes.

The second screenshot 204 provides simple instructions for a non-expert user 101 to analyze their blood oxygen levels on their own. As per the instructions, the user may be asked to hold the device 102 in the dominant hand (such as right hand) and point the camera at a fingernail on the non-dominant hand (left hand). The user may be given instructions to extend their index finger and place on a surface in their front. The instructions may ask the user to perform this test himself by squeezing the fingernail with one hand while holding the device 102 with the other hand. This can be done by placing the index finger on a table top, and covering the index fingernail with the middle finger, while holding the device 102 with the dominant hand.

The third screenshot 206 may illustrate an outline 214 on the display screen to guide the user to put their fingernail in right location. The outline 214 appears to show where to place the fingernail. Along with providing outline, the instructions may provide an estimated distance to be kept between the mobile computing device 102 and the fingernail. The estimated distance, may include, for example, 6 inches.

The fourth screenshot 208 illustrates that the user places a finger in front of a respective camera and aligns a view so that the finger is within the outline 214. In one embodiment of the present disclosure, the fourth screenshot 208 may include a "take picture" button (not shown) to enable a user to manually capture an image of the fingernail. In another embodiment of the present disclosure, the camera 103 is automatically configured to capture an image, when the finger is placed within the outline 214.

The fifth screenshot 210 is displayed upon capturing of the image, and includes a message that mentions that "Thank you, image is being analyzed. Please contact your healthcare provider for follow-up." While the message is displayed, the image is being analyzed either locally at the CNN processing unit 104 or at the server 107. The sixth screenshot 212 enables the user to move on to other features of the mobile application, such as other telehealth modules, or exit the mobile application.

Although, the mobile application is configured to detect cyanosis and measure CRT based on the analysis of captured images, it would be apparent to one of ordinary skill in the art, that other overall health monitoring application or diagnostic application may be integrated with the mobile application for diagnosis of other health conditions. For instance, the mobile application may be configured to analyze the face of the user to look for symptoms of flushing, redness, and perspiration, or it could be integrated into an application which gathers other health or wellness related data.

FIGS. 3A-3E illustrate a brief video stream used by the CNN processing unit 104 for measuring CRT of the user 101, in accordance with an embodiment of the present disclosure. The brief video stream includes a time series of images to estimate a curve of transition from a blanched state to a normal state of a fingernail of the user. In the context of the present disclosure, in the blanched state, the fingernail or fingertip is squeezed, removing the blood from the capillaries.

A first frame 301 of the video stream illustrates a fingernail 302 being compressed by an adjacent finger 304. The sequence is a CRT, which is a common test for peripheral blood circulation health by squeezing the fingernail 302 and observing as blood returns to the fingernail 302. In an example, the first frame 301 is captured at t=0 ms.

A second frame 306 shows the releasing of the fingernail 302, and color change in the fingernail 302. In an example, the second frame 306 is captured at t=367 ms and may be used for tracking rate of color change and track a location of the fingernail 302.

A third frame 308 shows that the blood is in the process of returning. In an example, the third frame 308 is captured at t=533 ms and may be used to continue tracking the location of the fingernail 302 and measuring blood content and coloration of the fingernail 302.

A fourth frame 310 shows that blood continues to return. In an example, the fourth frame 310 is captured at t=867 ms and may be used to continue tracking location of the fingernail 302 and measuring blood content and coloration of the fingernail 302.

A fifth frame 312 shows that the blood is returned to the fingernail 302 and a resting state has been achieved. In an example, the fifth frame 312 is captured at t=1533 ms, and may be used to track the rate of return of blood in the fingernail 302. In an embodiment of the present disclosure, a color plateau has been detected at the fifth frame 312, and the resting state may be analysed for cyanosis as well.

Figure 4:
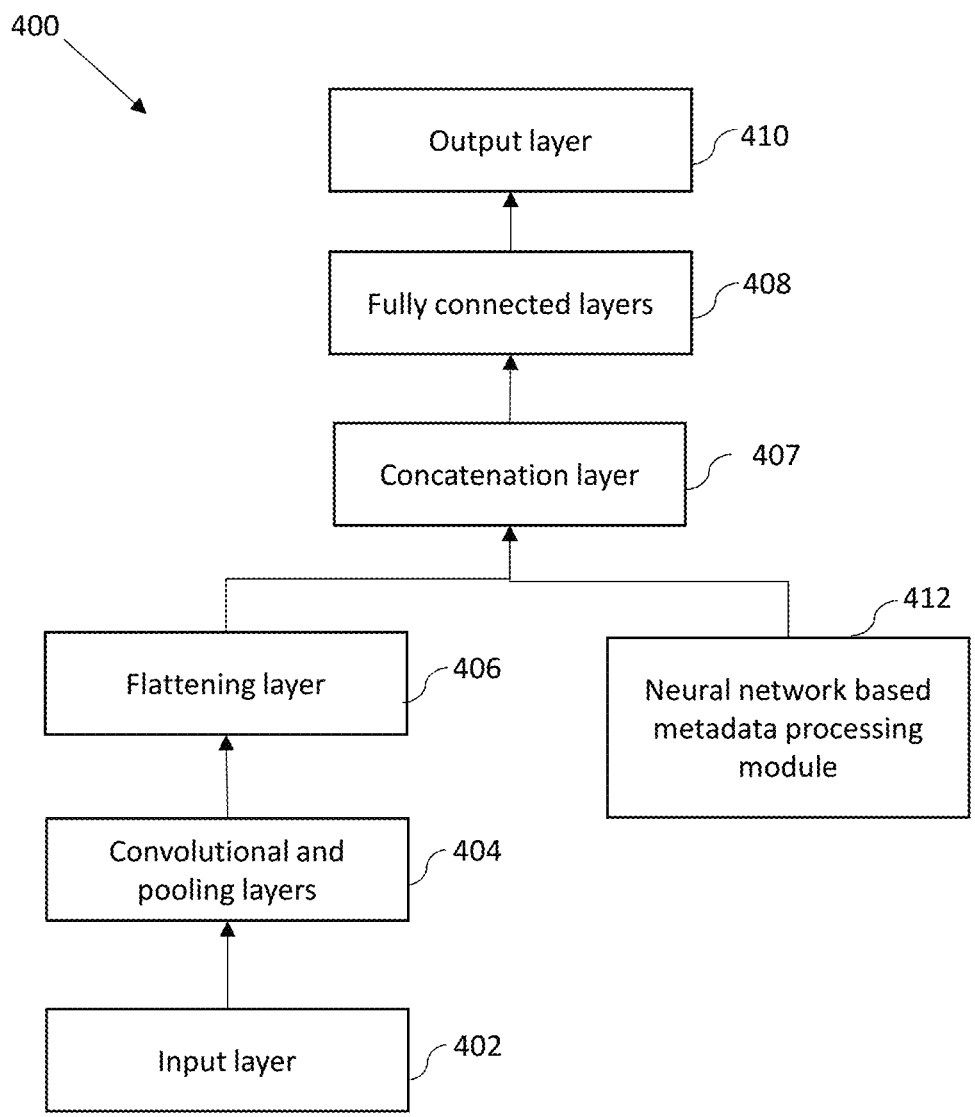
FIG. 4 illustrates a CNN used by the CRT measurement module and the cyanosis testing module for measuring CRT and detecting cyanosis, in accordance with an embodiment of the present disclosure.

FIG. 4 illustrates a CNN 400 implemented by the CNN processing unit 104 of FIG. 1 for measuring CRT and detecting cyanosis using images and videos detected by the camera 103 of FIG. 1, in accordance with an embodiment of the present disclosure. The CNN 400 includes an input layer 402, convolutional and pooling layers 404, a flattening layer 406, a concatenation layer 407, fully connected layers 408, and an output layer 410. The CNN 400 further includes a neural network based metadata processing module 412.

The input layer 402 receives an input image from the camera 103 of FIG. 1, in the form of a three dimensional tensor, with width, height, and color data. The convolutional and pooling layers 404 process the input image 401 to create two dimensional representations of features, such as edges and higher level combinations of features, and combine information from filter layers to reduce the spatial data. The flattening layer 406 remove the spatial relationships entirely, and generate data which is non-spatial.

The neural network based metadata processing module 412 is configured to receive a metadata vector for a patient that includes information from various sources, such as patient information (age, sex, weight, etc), health information (medical conditions), device information such as temperature, and image information such as Exchangeable image file format (EXIF) information, and camera settings, and convert the metadata vector into metadata. The metadata are non-spatial data.

The concatenation layer 407 is configured to concatenate non-spatial metadata with the non-spatial data generated by the flattening layer 406. The fully connected layers 408 are configured to map spatial features to output values, and learn the meaning of the features detected. The output layer 410 generates an output vector with at least two values, one for blood oxygenation level and the other indicating measurement confidence. The blood oxygenation value depends on the how the CNN 400 was trained. In an example, an output value of '1' for blood oxygenation level indicates positive detection of cyanosis, and an output value of '0' for blood oxygenation level means no detection of cyanosis. In the context of the present disclosure, the output value of blood oxygenation level may be provided in millimeters of mercury (mm Hg), which is the ordinary clinical unit of measurement of blood oxygen level. The blood oxygenation value generated by the CNN 400 might be a value that may be scaled, or transformed with a non-linear function, into conventional units such as mm Hg or may be unitless in some cases.

The output layer 410 further generates another output value indicating measurement confidence level, to determine if the measurement was successful or not. The success of measurement depends on correct positioning of the smartphone camera and the fingernail, usable levels of lighting, distance of fingernail from the camera. In an example, the fingernail might not even be present in the image captured by the camera due to incorrect positioning. In an embodiment of the present disclosure, when the mobile computing device 102 of FIG. 1 is a smartphone that is being provided with a predefined set of hyperparameters and a fast enough processor, it automatically captures a reading when the measurement confidence level is greater than or equal to a pre-defined threshold. When the measurement confidence level reaches the pre-defined threshold for a number of frames, the measurement is considered to be good, and when the measurement confidence level does not reach the pre-defined threshold, it may be inferred that the user has made a mistake, or there is some problem with the setting, such as light or other factors. In such case, the user may be provided with an assistance.

In an embodiment of the present disclosure, the CNN 400 applies the blood oxygenation value, and the measurement confidence level to a series of images generated by the camera 103 of FIG. 1 to measure the CRT of the user. The input image may be correlated with other sources of information, such as picture EXIF data, a temperature of the device 102, and self-reported other symptoms (such as shortness of breath) to derive an estimate of the CRT.

It may be noted that measurement of cyanosis, i.e. measurement of blood oxygenation levels is a static measurement, based on analysis of a single image, whereas measurement of CRT is an analysis of a series of images over time. The CRT value corresponds to that time instant at which blood presence in the fingernail bed has plateaued. The plateau corresponds to the resting state. Using the same CNN 400 for static measurement as well for detecting a plateau to measure CRT, has advantages of simplicity of system design.

In the context of the present disclosure, the number of layers and their configuration in the CNN 400 is determined through experimentation with a real training data corpus. The CNN 400 may be trained based on a dataset developed by capturing images of a user fingernail, and measuring oxygen levels using a conventional pulse oxygen meter in a clinical setting. The oxygen level is recorded along with the pictures and metadata. The CNN 400 may be further trained for the measurement confidence value, in which the training data include cases of poor capture, and images that don't even include a finger, and indicate those as invalid measurements. A skilled human may look at an image and evaluate the quality of the capture to estimate a measurement confidence level, which is either zero or one.

The training corpus for the CNN 400 may consist of a sufficiently large set of inputs and outputs as follows:

[image, metadata]→[blood oxygen level, confidence level]

Another view of the corpus, with an expanded set of metadata, would be: [image, white balance, patient age, patient gender, diabetes level, . . . ]→[blood oxygen mm Hg, confidence level]. The exposure and white balance information from the EXIF data and other camera sources may be used as data for training the CNN 400. Also, an ambient photo may be used to calibrate the detection. Also, cold temperatures may also result in reduced blood flow to the extremities, so the corresponding temperature sensor may be used in the calculations to calibrate for cold conditions.

It can be seen that the corpus of training data requires both images, and metadata as inputs, and generate outputs as blood oxygen (mm Hg) and confidence values. The corpus of training data may be generated using individuals in a data capture process, using a training application running on real smartphones, and in a clinical setting. The training application may have a UI which may be nearly identical to the GUI 106 of FIG. 1.

It would be apparent to one of ordinary skill in the art, that the CNN 400 may including Recurring Neural Networks (RNNs) such as Long Short-Term Memories (LSTMs) and Gated Recurrent Units (GRUs) for analyzing time series images. The training corpus may be created for not just static images, but for a series of images.

Figure 5A:
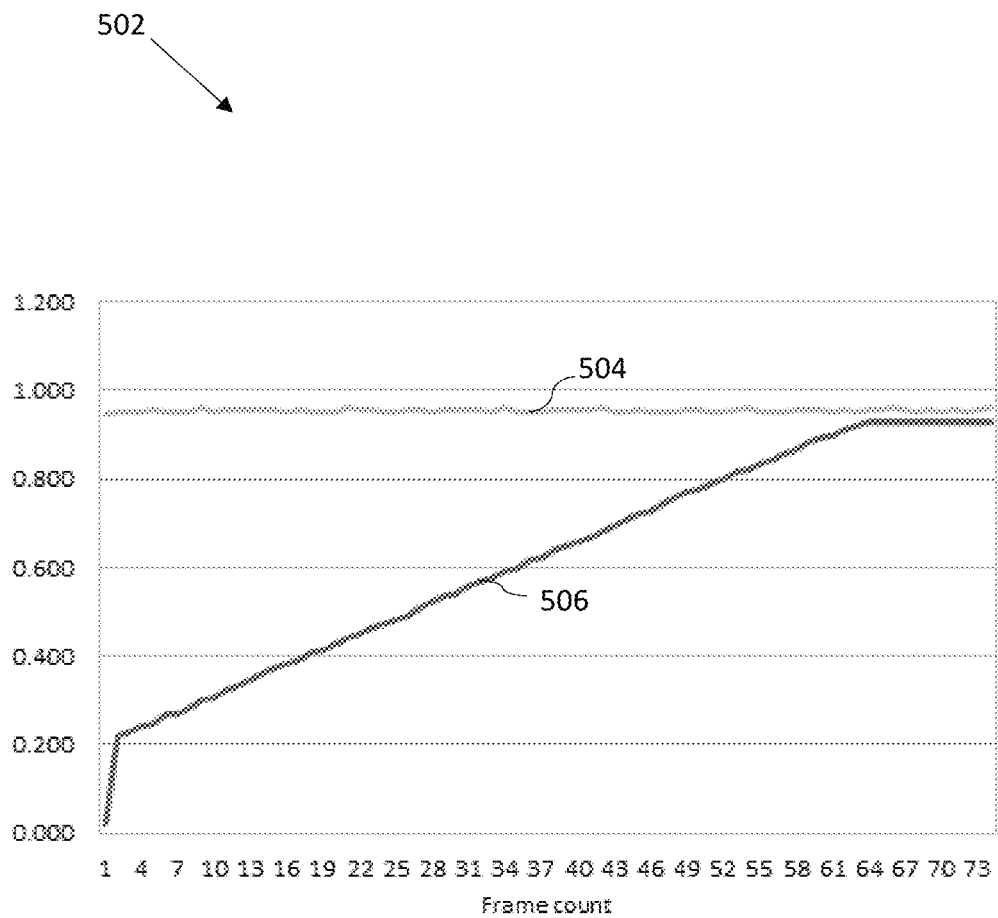
FIGS. 5A-5C are first, second and third graphs for illustrating simulated data pertaining to CRT measurements over a time period of two seconds respectively.

FIG. 5A is a first graph 502 illustrating simulated data pertaining to successful CRT measurement of a healthy individual over two seconds, when the frame capture rate is assumed to be 30 frames per second. The graph 502 includes a first line 504 that represents measurement confidence value over time, and a second line 506 that represents confidence value measured over time. At t=0, the finger is in the blanched state, and as image frame size increases, the oxygen content increase over subsequent frames until it reaches a plateau at the image frame number 65. The time instant corresponding to the image frame number 65 is referred to as $t_{normal}$ and is hereinafter referred to as a corresponding CRT value. In an individual without a peripheral circulatory problem, the $t_{normal}$/CRT value would be approximately 2 to 3 seconds.

Figure 5B:
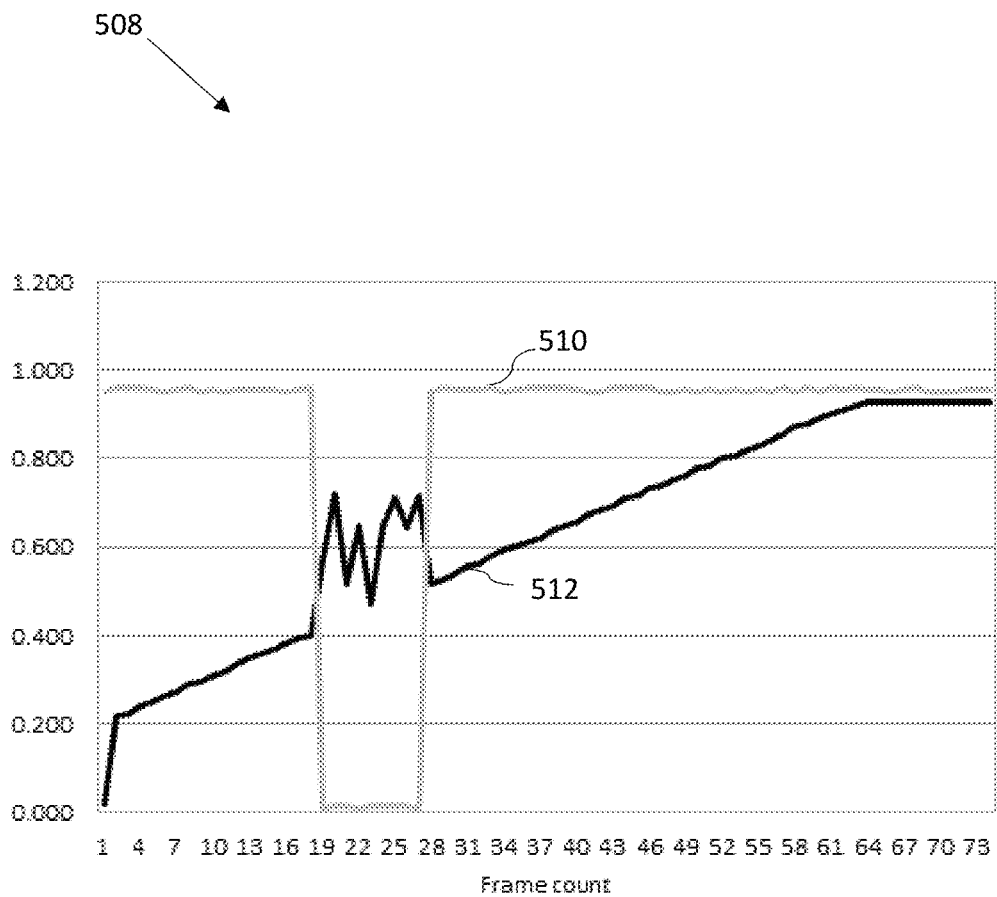

FIG. 5B is a second graph 508 illustrating simulated data pertaining to unsuccessful CRT measurement over two seconds, when the frame capture rate is 30 frames per second. The first line 510 represents measurement confidence value that dropped from frame 18 to frame 26 below 0.9 due to a sudden movement of the camera, or a loss of ambient light, or some other user error. During the set of frames when the measurement confidence level is low, the CNN 400 continues to output a value for oxygenation (represented by the second line 512), however this value is not meaningful. The user may be informed about the same in corresponding user interface, with a relevant message such as, "The measurement was invalid. Please repeat the measurement, and ensure that the camera and finger do not move during the measurement."

Figure 5C:
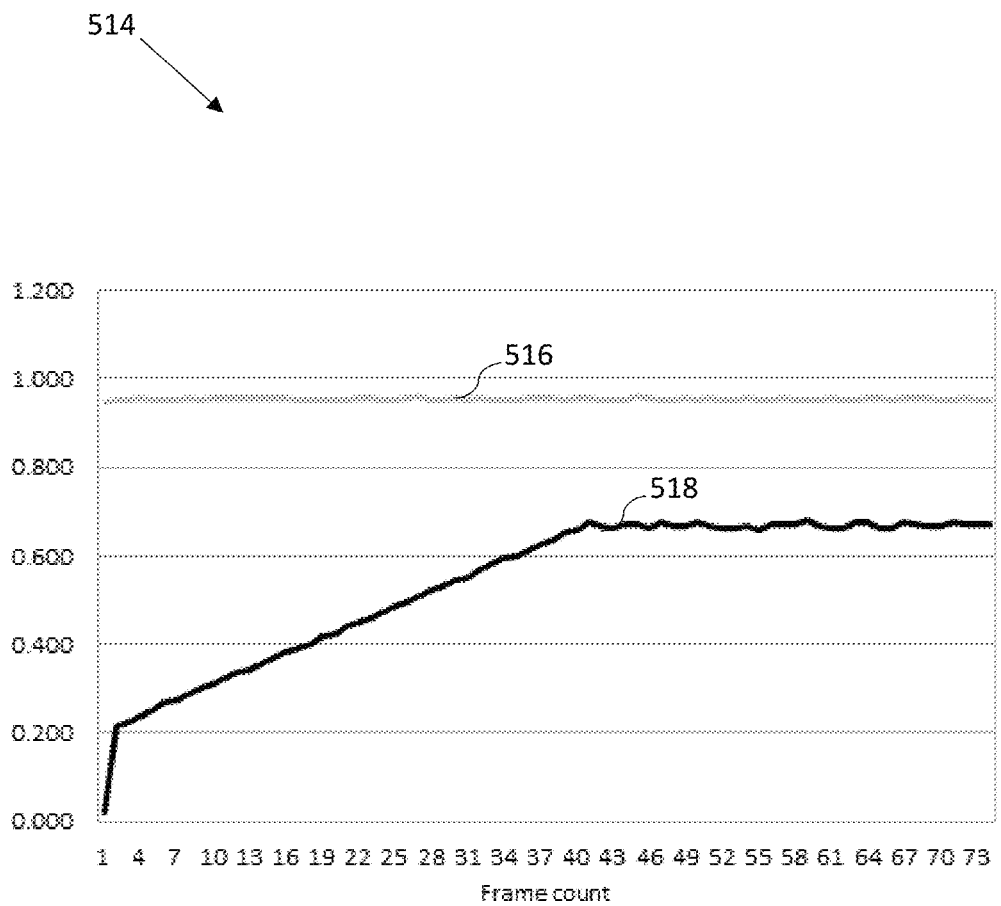

FIG. 5C is a third graph 514 illustrating simulation results corresponding to successful CRT measurement of an unhealthy individual over two seconds. As shown, the measurement confidence level (represented by the first line 516) remains high throughout, which means that the measurement is valid. Within the measurement time, the blood oxygenation value (represented by the second line 518) never returns to a healthy level. This indicates an abnormal CRT measurement and the system alerts the individual to contact a clinician, or may automatically send this result to a clinician, to determine an appropriate follow-up.

In an embodiment of the present disclosure, a rate of refill may be determined for a fingernail returning from blanched to normal state. Human clinicians today use CRT as a pass/fail test for peripheral circulatory health, due to limitations in human observation of rapid and subtle color change. In contrast, by measuring blood levels frame by frame, the velocity of refill may be measured by estimating the slope of the line from blanched state to resting state. More accurate measurement of the dynamics of CRT may lead to clinical insights. The rate of refill may differ from one person to another due to subtle variations in its velocity, resulting in different curves of return.

Figure 6:
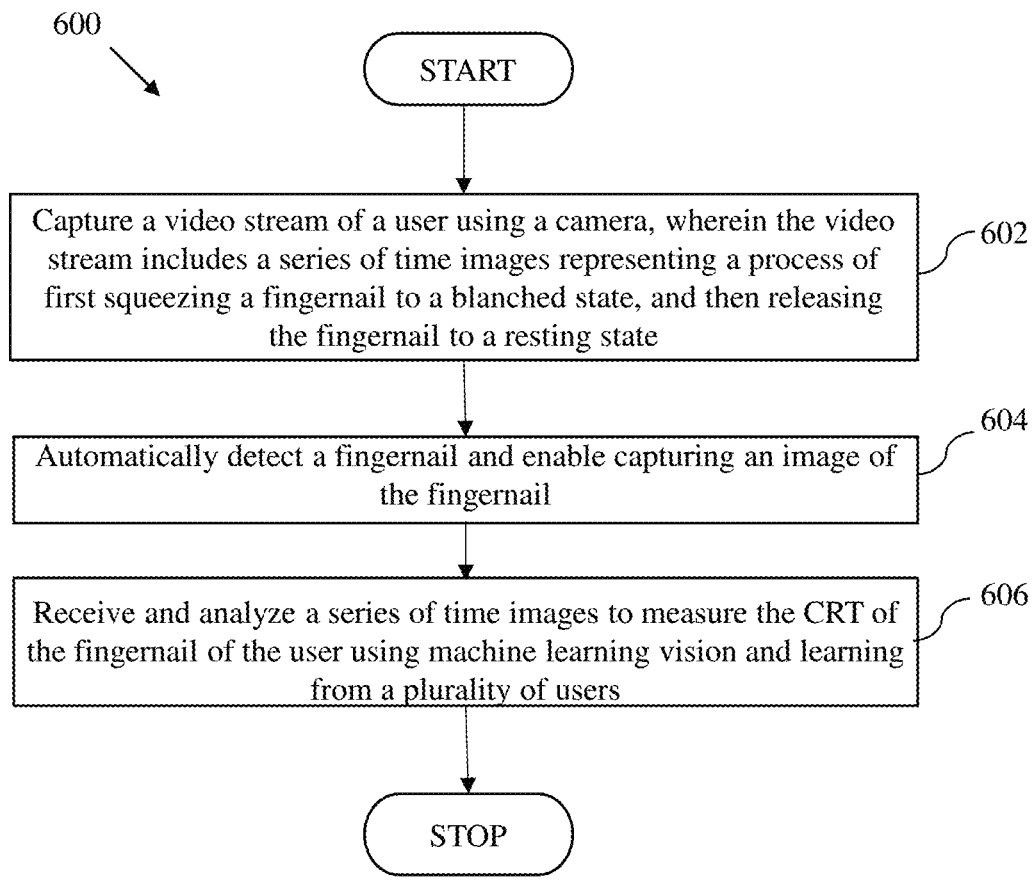
FIG. 6 is a flow chart to illustrate a method for measuring blood oxygen levels and CRT of a user, in accordance with an embodiment of the present disclosure.

FIG. 6 is a flow chart to illustrate a method 600 for measuring CRT of the user using a mobile computing device, in accordance with an embodiment of the present disclosure.

At step 602, a video stream of a user is captured using a camera. The video stream includes a series of images representing a process of first squeezing a fingernail to a blanched state, and then releasing the fingernail to a resting state.

At step 604, a fingernail is automatically detected, and an image of the fingernail is captured. In an embodiment of the present disclosure, a graphical user interface (GUI) is provided on a display screen of the mobile computing device, wherein the GUI illustrate an outline on the display screen to guide the user to put their fingernail in right location. In another embodiment of the present disclosure, the image of the fingernail and one or more regions within the fingernail image are identified to correlate visual features of the one or more regions with blood oxygen levels of the user to detect cyanosis, wherein cyanosis causes blood to become bluish in color.

At step 606, a series of images is received and analyzed to measure the CRT of the fingernail of the user using machine learning vision and learning from a plurality of users, wherein measuring the CRT comprises estimating a curve of transition from the blanched state to the resting state of the fingernail. In an embodiment of the present disclosure, a position of the fingernail is determined to detect tracking rate of color change of the fingernail, and measure a blood content and coloration of the fingernail. In another embodiment of the present disclosure, the CRT measurement is performed using the same CNN as used in cyanosis detection, but over a time series of images to create a graph of blood return from the blanched to the resting state. In yet another embodiment of the present disclosure, the image EXIF data, a temperature sensor data of the mobile computing device, and patient information along with the series of images is analyzed to generate an output value of CRT, wherein the image EXIF data is metadata from the camera which includes white balance and other photograph parameters.

As will be appreciated by those ordinary skilled in the art, the method steps may be implemented by suitable code on a processor base system, such as general purpose or special purpose computer (i.e., machine). It should also be noted that different implementations of the present technique may perform some or all the steps described herein in different orders or substantially concurrently, that is, in parallel. Furthermore, the functions may be implemented in a variety of programming languages. Such code, as will be appreciated by those of ordinary skilled in the art, may be stored or adapted for storage in one or more tangible non-transitory machine readable media, such as on memory chips, local or remote hard disks, optical disks or other media, which may be accessed by a processor based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in a computer memory.

A person having ordinary skill in the art will appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor and a memory may be used to implement the above described embodiments. Further, the operations may be described as a sequential process, however some of the operations may in fact be performed in parallel, concurrently, and/or in a distributed environment, and with program code stored locally or remotely for access by single or multiprocessor machines. In addition, in some embodiments the order of operations may be rearranged without deviating from the scope of present disclosure.

While various embodiments of the present disclosure have been illustrated and described, it will be clear that the present disclosure is not limited to these embodiments only. Numerous modifications, changes, variations, substitutions, and equivalents will be apparent to those skilled in the art, without departing from the spirit and scope of the present disclosure, as described in the claims.

The invention claimed is:

1. A system for measuring blood oxygenation levels and capillary refill time (CRT) of a user using a mobile computing device, comprising:
   a camera configured to capture a video stream of a user, wherein the video stream includes a series of images representing a process of first squeezing a fingernail of the user to a blanched state, and then releasing the fingernail to a resting state;
   a Convolutional Neural Network (CNN) based processing unit that includes a pre-trained CNN that comprises:
      an input layer configured to receive one or more input images from the camera;
      a plurality of convolutional and pooling layers configured to process an input image to create a two-dimensional representation of one or more features;
      a flattening layer configured to remove spatial relationships in the two-dimensional representation and generate non-spatial data;
      a neural network based metadata processing module configured to generate non-spatial metadata for the user based on a metadata vector;
      a concatenation layer configured to concatenate non-spatial metadata with the non-spatial data generated by the flattening layer;
      a plurality of fully connected layers configured to:
         identify the fingernail in the resting state, and one or more regions within a static image of the fingernail, and
         correlate one or more non-spatial features with one or more pre-defined blood oxygenation values;
      an output layer configured to:
         generate a blood oxygenation value indicating blood oxygenation levels in the user, and determine if measurement from the series of images by the camera is successful by generating a measurement confidence level and comparing the measurement confidence level with a pre-defined threshold to indicate success of measurement if, based on the comparison, the measurement confidence level is greater than or equal to the pre-defined threshold; and generate a CRT value of the user by applying the blood oxygenation value, and the measurement confidence level to the series of images captured by the camera over time, wherein the CRT corresponds to time lapsed from the blanched state to the resting state of the fingernail; and an output display device for displaying the blood oxygenation and CRT values to the user, and generating one or more pre-defined alerts corresponding to the displayed blood oxygenation and CRT values.

2. The system of claim 1, wherein the CNN is configured to detect a position of the fingernail to track a location of the fingernail, track a rate of return of blood in the fingernail, track a rate of color change of the fingernail, and measure a blood content and coloration of the fingernail during color change.

3. The system of claim 1, wherein the CNN is configured to automatically detect a fingernail and enable capturing an image of the fingernail by the camera.

4. The system of claim 1, wherein the metadata vector includes age, sex, weight, and medical conditions of the user, a room temperature, an image EXIF data, and camera settings of the camera, wherein the image EXIF data is metadata from the camera which includes white balance and other photograph parameters.

5. The system of claim 1, wherein the CNN is configured to analyze the one or more input images to identify symptoms of at least one of: COVID-19, shock, dehydration, sepsis and hypothermia.

6. The system of claim 1 further comprising a graphical user interface (GUI) provided on a display screen of the mobile computing device, wherein the GUI illustrates an outline on the display screen to guide the user to put their fingernail at a pre-defined location.

7. The system of claim 1, wherein the CNN is configured to detect Carbon monoxide (CO) poisoning in the user based on an image of the fingernail in the resting state, wherein carbon monoxide poisoning causes blood to become excessively red.

8. The system of claim 1, wherein the measurement confidence level is determined based on a positioning of the camera relative to the fingernail, a level of lighting incident on the fingernail, and a distance of the fingernail from the camera.

9. The system of claim 1, wherein the CNN is trained based on a dataset developed by capturing one or more images of a user fingernail, and measuring oxygen levels using a conventional pulse oxygen meter in a clinical setting.

10. A method for measuring blood oxygenation levels and capillary refill time (CRT) of a user using a mobile computing device, the method comprising:

capturing a video stream of a user, wherein the video stream includes a series of images representing a process of first squeezing a fingernail of the user to a blanched state, and then releasing the fingernail to a resting state;

receiving one or more input images by an input layer of a Convolutional Neural Network (CNN);

processing an input image to create a two-dimensional representation of one or more features;

removing spatial relationships in the two-dimensional representation and generate non-spatial data;

generating non-spatial metadata for the user based on a metadata vector;

concatenating the non-spatial metadata with the non-spatial data;

identifying the fingernail in the resting state, and one or more regions within a static image of the fingernail, and correlating one or more image features with one or more pre-defined blood oxygenation values;

generating a blood oxygenation value indicating blood oxygenation levels in the user, and determining if measurement from the series of images by the camera is successful by generating a measurement confidence level and comparing the measurement confidence level with a pre-defined threshold to indicate success of measurement if, upon comparison, the measurement confidence level is greater than or equal to the pre-defined threshold;

generating a CRT value of the user by applying the blood oxygenation value, and the measurement confidence level to the series of images captured by the camera over time, wherein the CRT corresponds to time lapsed from the blanched state to the resting state of the fingernail; and displaying the blood oxygenation and CRT values to the user, and generating one or more pre-defined alerts corresponding to the displayed blood oxygenation and CRT values.

11. The method of claim 10 further comprising detecting a position of the fingernail to track a location of the fingernail, track a rate of return of blood in the fingernail, track a rate of color change of the fingernail, and measure a blood content and coloration of the fingernail during color change.

12. The method of claim 10 further comprising automatically detecting a fingernail and enabling capturing an image of the fingernail by the camera.

13. The method of claim 10, wherein the metadata vector includes age, sex, weight, and medical conditions of the user, a room temperature, an image EXIF data, and camera settings of the camera, wherein the image EXIF data is metadata from the camera which includes white balance and other photograph parameters.

14. The method of claim 10 further comprising analyzing the one or more input images to identify symptoms of at least one of: COVID-19, shock, dehydration, sepsis and hypothermia.

15. The method of claim 10 further comprising providing a GUI that illustrates an outline on the display screen to guide the user to put their fingernail at a pre-defined location.

16. The method of claim 10 further comprising detecting Carbon monoxide (CO) poisoning in the user based on an image of the fingernail in the resting state, wherein carbon monoxide poisoning causes blood to become excessively red.

17. The method of claim 10, wherein the measurement confidence level is determined based on a positioning of the camera relative to the fingernail, a level of lighting incident on the fingernail, and a distance of the fingernail from the camera.

18. A non-transitory computer readable medium having stored thereon executable instructions that when executed by a processor configures the processor to measure blood oxygenation levels and capillary refill time (CRT) by:

capturing a video stream of a user, wherein the video stream includes a series of images representing a process of first squeezing a fingernail of the user to a blanched state, and then releasing the fingernail to a resting state;

receiving one or more input images by an input layer of a Convolutional Neural Network (CNN);

processing an input image to create a two-dimensional representation of one or more features;

removing spatial relationships in the two-dimensional representation and generate non-spatial data;

generating non-spatial metadata for the user based on a metadata vector;

concatenating the non-spatial metadata with the non-spatial data;

identifying the fingernail in the resting state, and one or more regions within a static image of the fingernail, and correlating one or more non-spatial features with one or more pre-defined blood oxygenation values;

generating a blood oxygenation value indicating blood oxygenation levels in the user, and determining if measurement from the series of images by the camera is successful by generating a measurement confidence level and comparing the measurement confidence level with a pre-defined threshold to indicate success of measurement if, based on the comparison, the measurement confidence level is greater than or equal to the pre-defined threshold;

generating a CRT value of the user by applying the blood oxygenation value, and the measurement confidence level to the series of images captured by the camera over time, wherein the CRT corresponds to time lapsed from the blanched state to the resting state of the fingernail; and displaying the blood oxygenation and CRT values to the user, and generating one or more pre-defined alerts corresponding to the displayed blood oxygenation and CRT values.

19. The non-transitory computer readable medium of claim 18, wherein, upon execution of the instructions, the processor is configured to detect a position of the fingernail to track a location of the fingernail, track a rate of return of blood in the fingernail, track a rate of color change of the fingernail, and measure a blood content and coloration of the fingernail during color change.

* * * * *